United States Patent [19]

McNamara

[11] 4,178,916
[45] Dec. 18, 1979

[54] DIABETIC INSULIN ALARM SYSTEM

[76] Inventor: Elger W. McNamara, 5520 W. Camino Cielo, Santa Barbara, Calif. 93105

[21] Appl. No.: 836,250

[22] Filed: Sep. 26, 1977

[51] Int. Cl.$^2$ ................................................ A16B 5/4
[52] U.S. Cl. .................................... 128/734; 128/736
[58] Field of Search ............. 128/2.1 A, 2.05 R, 2 R, 128/ 2 H, 2.1 Z

[56] References Cited

U.S. PATENT DOCUMENTS

| | | | |
|---|---|---|---|
| 3,478,344 | 11/1969 | Schwitzgebel et al. | 128/2.1 A |
| 3,572,316 | 3/1971 | Vogelman et al. | 128/2.1 A |
| 3,870,034 | 3/1975 | James | 128/2.1 Z |
| 3,902,478 | 9/1975 | Konopasek et al. | 128/2.1 A |
| 3,937,004 | 2/1976 | Natori et al. | 128/2.1 A |
| 3,972,320 | 8/1976 | Kalman | 128/2.1 A |

FOREIGN PATENT DOCUMENTS

1008027  10/1965  United Kingdom .................. 128/2.1 A

OTHER PUBLICATIONS

Beerwinkle, K. R. et al., "A Low-Power Combination ECG-Respiration Telemetry Transmitter," IEEE Trans. on Biomed. Engr. vol. BME-23 No. 6 pp. 484-486, Nov. 1976.
Harrison, W. T., "Principles of Internal Medicine," McGraw Hill Pub., N.Y. 1974 p. 545.

*Primary Examiner*—Robert W. Michell
*Assistant Examiner*—Francis J. Jaworski
*Attorney, Agent, or Firm*—Spensley, Horn & Lubitz

[57] ABSTRACT

The disclosed Diabetic Insulin Alarm System is designed to monitor certain physiological conditions of the wearer associated with insulin shock. The system includes means to sense such physiological conditions of the wearer and to produce an electrical output. This output actuates a pulse generator which in turn energizes an oscillator producing oscillations that are applied both to an enclosed speaker and to a tuned circuit. The tuned circuit, in turn, energizes an antenna which radiates electromagnetic energy at a frequency to which an electromagnetic receiver may be tuned. Thus, by tuning an electromagnetic receiver, such as a radio, to the frequency radiated by the antenna, a wearer can employ the receiver to alert him to the onset of insulin shock, the audible tone produced by the speaker even waking him when asleep.

9 Claims, 5 Drawing Figures

DIABETIC INSULIN ALARM SYSTEM

A Diabetic Insulin Alarm System is described, particularly one designed to be worn by a person and to alert him through a conventional radio receiver to physiological conditions associated with insulin shock.

For certain human ailments, it is necessary for one to be able to continuously monitor his own condition. When awake, often it is possible for one to consciously do this himself, but when asleep, that is not possible. Since people normally sleep six to eight hours, it is essential to provide them with the capability of monitoring their physiological condition and to wake them, should their condition become abnormal. This invention provides such a capability.

As a preferred example of the invention, it is necessary for diabetic people periodically to take insulin. If they wait too long, or take too much, serious physiological disturbances develop. Also, since one's metabolic rate varies from time to time, even if a diabetic person takes a proper dosage of insulin at proper intervals, he still can experience physiological disorders. His temperature, pulse rate, and skin resistance all will exhibit abnormalities as insulin shock develops. Accordingly, an important object of the invention is to provide a system that can be worn by a diabetic person, the system responding to the wearer's abnormal skin resistance, or temperature, or both as insulin shock develops, and signalling this condition to the wearer, should he be asleep. These, and other objects of the invention, will be apparent to those skilled in this field from the following description of a preferred embodiment.

BRIEF SUMMARY OF THE INVENTION

The disclosed Diabetic Insulin Alarm System is designed to be worn on a person's limb, particularly about the wrist, and to monitor at least one physiological condition of the wearer associated with insulin shock. Psychological conditions associated with insulin shock include lowered skin resistance, a drop in body temperature, a reduced ability to respond to light changes (eye pupil dialation lag) and, in heavy shock, increased heart beat, labored breathing and convulsions. If allowed to develop, such shock can lead to a heart attack and death.

The system includes means to sense such a physiological condition of the wearer and to produce an electrical output should such condition become abnormal. Pulse generating means are actuated by the output of the sensing means to generate pulses. Oscillator means, actuated by generated pulses of a given polarity, feed a tuned circuit. Antenna means are connected to the tuned circuit to radiate electromagnetic energy at a frequency detectable by an electromagnetic receiver. Thus, should the wearer's physiological condition become abnormal, electromagnetic energy radiated by the antenna means will be received by the electromagnetic receiver, its output in turn alerting the wearer to such an abnormal physiological condition.

Preferably, the system includes switch means to manually energize the pulse generator, thereby permitting the wearer to tune any of various conventional electromagnetic receivers to the frequency of the radiation broadcast by the antenna means. Also, preferably the system includes either visual or audible signal generators, or both, responsive to the output of the sensor means to alert the wearer to an abnormal condition independent of the electromagnetic receiver. Further, preferably the system senses multiple physiological conditions of the wearer, including the wearer's skin resistance and temperature, either or both of which, when abnormal, cause the system to produce an electrical output to actuate the pulse generator.

BRIEF DESCRIPTION OF THE DRAWING

The invention will be further described in connection with the accompanying drawing in which.

DETAILED DESCRIPTION

Figure 1:
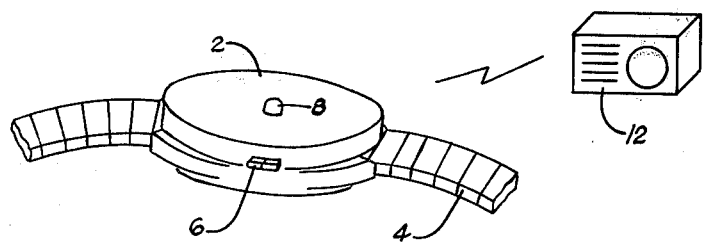
FIG. 1 is a perspective view of the system and an associated electromagnetic receiver.

Preferably the system for monitoring a person's vital signs in encased in a unit small enough to be worn about the limb of a person, such as about the wearer's wrist. As indicated in FIG. 1, the system is received within a case, or housing 2, to which is connected a band or strap 4 (illustrated as being partially broken away) the band securing the case about the wrist of the wearer.

The system includes a switch, 6, for manual actuation of the electronic system. It also preferably includes an element 8 that radiates light when an abnormal physiological condition is sensed by the system to alert the wearer. The system is designed to radiate electromagnetic energy to a nearby electromagnetic receiver 12, such as an FM radio receiver, which may be tuned to such radiation. Thus, when the system senses an abnormal physiological condition of the wearer, electromagnetic energy is radiated, causing the receiver 12 to produce an audible sound corresponding to the nature of the radiated energy. By adjusting the volume of the receiver, this audible signal will wake the wearer even if he is asleep.

Figure 2:
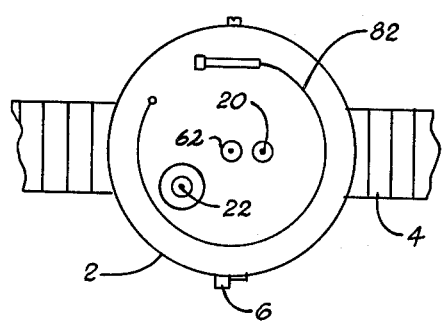
FIG. 2 is a plan view of the underside of the system's case.

As best shown in FIG. 2, preferably the system includes a set of probes 20, that project through openings in the bottom of case 2, to contact the skin of the wearer and sense changes in skin resistance. The unit also includes a thermistor 22, which also projects through an opening in the bottom of case 2 to contact the skin of the wearer, this sensor being responsive to changes in skin temperature.

Figure 3:
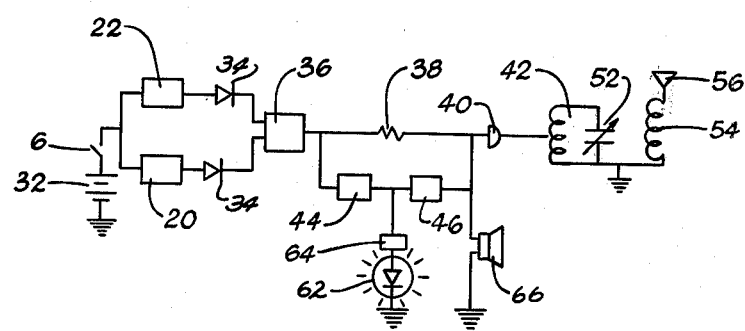
FIG. 3 is a block diagram of a preferred electrical system.

FIG. 3 presents a block diagram of a preferred design of the electronic portion of the Diabetic Insulin Alarm System. Both the skin resistance sensor 20 and the temperature sensor 22, are connected through switch 6 to a source of electrical power 32, such as a battery. The outputs of both of these sensors are supplied through amplifiers and diodes 34 to a pulse generator 36, the output of both sensors being required to cause the pulse generator to generate a train of pulses. This train of pulses is, in turn, applied through a loading resistance 38, and a tunnel diode 40, to a tuned circuit 42. The pulse train also is supplied to an oscillator 44, which, in response, generates an sinusoidal electrical signal of a frequency of, for example, 1000 hz. The signal is amplified by amplifier 46 and also supplied to tunnel diode 40. Thus, the tuned circuit 42 receives both a pulse train of a frequency of about 0.7 hz. per second and, for one-half of the pulse cycle, it also receives an oscillating electromagnetic signal.

The tuned circuit 42 is adjusted, by means of variable capacitor 52, to oscillate at rate that is detectable by the radio receiver 12. For example, if the radio receiver is an FM receiver, the tuned circuit 42 may be adjusted to a frequency of between 88 and 110 mhz. These oscillations induce sympathetic oscillations in inductor 54, which is magnetically coupled to the inductor of the tuned circuit 42. This inductor energizes antenna 56, causing it to broadcast electromagnetic radiations at the frequency of tuned circuit 42, these radiations preferably consisting of bursts of 1,000 hz. electromagnetic energy. They produce in receiver 12 a pulsating tone signal.

A light emitting diode 62 may be connected to be energized by the signal produced by oscillator 44 as, for example, through a field effect transistor 64. Alternately, the light emitting diode may be connected to the output of amplifier 46. Also, there may be connected to the output of amplifer 46, a loud speaker 66, this loud speaker being incorporated within case 2, to further alert the wearer to an abnormal psychological condition. Light emitting diode 62 preferably is exposed at the center of the face of case 2 (as element 8) to visually alert the wearer to an abnormal psychological condition.

Preferably, the temperature sensor 22 is adjustable and can be set by the wearer, or by his medical consultant, to be actuated by a temperature which, for him, is abnormal. This feature is particularly desirable since different wearers will have significantly different normal wrist temperatures. The skin resistor sensor 20 is simply a set of probes that are spaced a given distance apart, as illustrated in FIG. 2, the probes being connected through the skin of the wearer and thus sensing the wearer's skin resistance.

Particularly in high humidity areas, it is desirable to require both an abnormal temperature and an abnormal skin resistance for actuation of the pulse generator. This can be achieved simply by incorporating an "and" gate in the pulse generator's input circuit. Also, it is desirable to be able to adjust the sensor to respond to an abnormal change in the physiological condition of the wearer, whether it be an increase in value or a decrease in value. By simply reversing the leads to the source amplifiers (FIG. 4), the preferred electronic circuit may be made to respond to either a drop in temperature or skin resistance or an increase in temperature or skin resistance.

Figure 4:
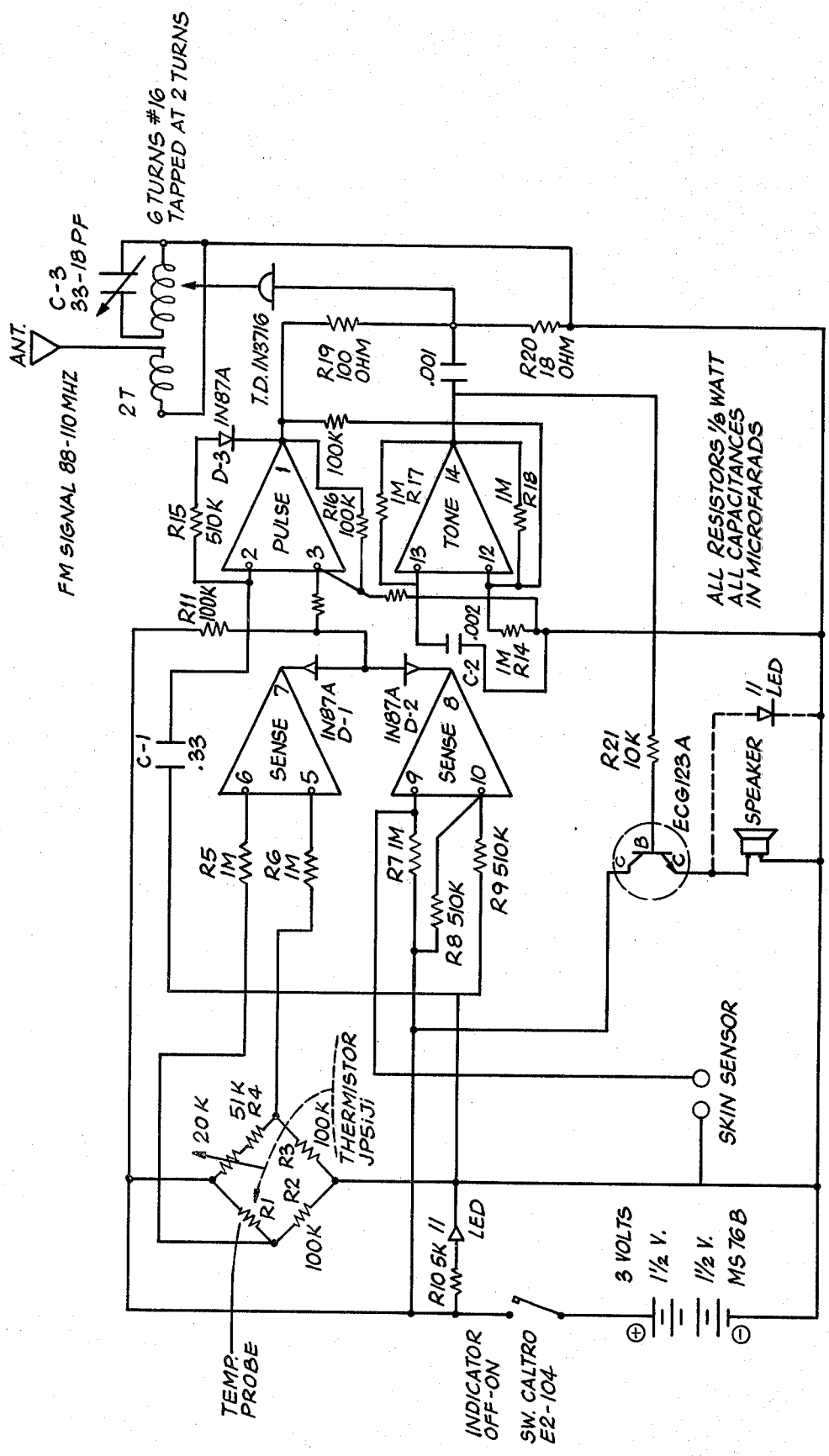
FIG. 4 is an electrical schematic of the preferred system.

Illustrated in FIG. 4 is a detailed schematic diagram of a preferred electrical circuit incorporating elements which correspond to the blocks illustrated in the block diagram presented in FIG. 3. It also includes the characteristics of the preferred components. All resistors have a 10% tolerance and are either of 1/16th or ⅛th watt capacity. The capacitor values are indicated in micro farads. The four integrated circuits are all incorporated in a single component, which preferably is an ICLM 324.

Figure 5:
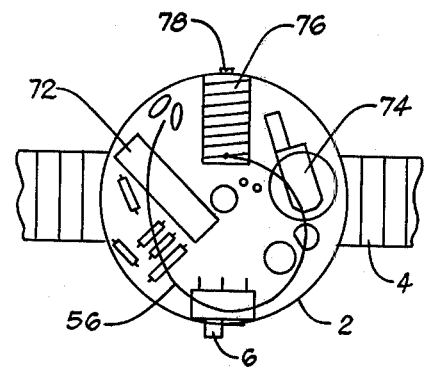
FIG. 5 is a plan view of the system in its case with the cover removed.

FIG. 5 illustrates the case housing the system with the cover removed, and shows the preferred layout of the various electrical components included in the preferred circuit. Among these components are the integrated circuit 72, the battery 74, the tuned circuit 76, with an adjustment screw 78 for the capacitor 52 projecting beyond the case, the light emitting diode 62, and switch 6. The antenna 56 preferably is simply a loop of wire, as illustrated. Also, preferably this antenna is loaded by a corresponding loop 82 (illustrated in FIG. 2) that is applied about the base of the case and which is insulated both from the case and from the wearer.

While a preferred embodiment of the invention has been described and illustrated, variations will be apparent to those skilled in this field. Accordingly, the scope of the invention is set forth in the following claims.

I claim:

1. A diabetic shock alarm system designed to be worn on a person's wrist and to monitor the wearer's body temperature and skin resistance, signalling to the wearer the onset of diabetic shock, the system including:

Means to sense the body temperature of the wearer and to produce an electrical output, Means to sense the skin resistance of the wearer and to produce an electrical output, Pulse generator means actuated by an abnormal output of both the body temperature sensor means and the skin resistance sensor means to generate pulses only in response to an abnormal output of said sensor means, Oscillator means actuated by pulses of a given polarity produced by the pulse generator, A tuned circuit directly connected to both the pulse generator means and the oscillator means to be energized by both the pulses produced by the pulse generator and oscillations produced by the oscillator means, and Antenna means connected to the tuned circuit to radiate electromagnetic energy at a frequency of an electromagnetic receiver, whereby the wearer may tune the electromagnetic receiver to the frequency of the tuned circuit, the system then alerting the wearer of the onset of diabetic shock through the electromagnetic receiver.

2. A system as set forth in claim 1 including switch means to manually energize the pulse generator means, permitting the wearer to tune the electromagnetic receiver to the frequency of the electromagnetic radiation broadcast by the antenna means.

3. A system as set forth in claim 1 including a visual signal generator responsive to the output of the sensor means to visually alert the wearer to an abnormal physiological condition.

4. A system as set forth in claim 1 including an audible signal generator responsive to the output of the sensor means to audibly alert the wearer to an abnormal physiological condition.

5. A system as set forth in claim 1 including means to adjust the frequency of the electromagnetic energy radiated by the antenna means.

6. A system as set forth in claim 1 including means to electromagnetically load the antenna means.

7. A system as set forth in claim 1 including switch means to manually energize the pulse generator, permitting the wearer to tune the electromagnetic receiver to the frequency of the electromagnetic energy broadcast by the antenna, the system further including signal generator means responsive to the output of the sensor means to alert the wearer to an abnormal physiological condition independent of the electromagnetic receiver, and means to adjust the frequency of the electromagnetic signals radiated by the antenna.

8. A system, as set forth in claim 7, in which at least one of the sensor means is adjustable.

9. A system as set forth in claim 1 in which at least one of said sensor means is adjustable.

* * * * *